United States Patent
Atarashi et al.

(10) Patent No.: US 9,826,728 B2
(45) Date of Patent: Nov. 28, 2017

(54) INSECT PEST CONTROL AGENT

(71) Applicants: EARTH CHEMICAL CO., LTD., Chiyoda-ku, Tokyo (JP); HONEYWELL INTERNATIONAL INC., Morristown, NJ (US)

(72) Inventors: Mikihiko Atarashi, Hyogo (JP); Akira Matsubara, Hyogo (JP); Ren Abe, Hyogo (JP)

(73) Assignees: HONEYWELL INTERNATIONAL INC., Morris Plains, NJ (US); EARTH CHEMICAL CO., LTD., Tokyo (JP)

( * ) Notice: Subject to any disclaimer, the term of this patent is extended or adjusted under 35 U.S.C. 154(b) by 420 days.

(21) Appl. No.: 14/406,292

(22) PCT Filed: Jun. 7, 2013

(86) PCT No.: PCT/JP2013/065796
§ 371 (c)(1),
(2) Date: Dec. 8, 2014

(87) PCT Pub. No.: WO2013/183754
PCT Pub. Date: Dec. 12, 2013

(65) Prior Publication Data
US 2015/0173342 A1    Jun. 25, 2015

(30) Foreign Application Priority Data
Jun. 8, 2012    (JP) .................................. 2012-131329

(51) Int. Cl.
*A01M 7/00*    (2006.01)
*A01N 29/02*    (2006.01)

(52) U.S. Cl.
CPC ........ *A01M 7/0003* (2013.01); *A01M 7/0017* (2013.01); *A01N 29/02* (2013.01)

(58) Field of Classification Search
CPC .... A01M 7/0003; A01M 7/0017; A01N 29/02
See application file for complete search history.

(56) References Cited

U.S. PATENT DOCUMENTS 6,713,518 B1 *    3/2004    Bessette .................. A01N 25/08
424/DIG. 11
2009/0041677 A1    2/2009    Singh et al.
(Continued)

FOREIGN PATENT DOCUMENTS

| EP | 2179649 A1 | 4/2010 |
|----|------------|--------|
| JP | 62-132803 A | 6/1987 |

(Continued)

OTHER PUBLICATIONS

Extended Search Report dated Dec. 4, 2015; Appln. No. 13801079.8-1454 / 2862441.

*Primary Examiner* — Gary C Hoge
(74) *Attorney, Agent, or Firm* — Colleen D. Szuch

(57) ABSTRACT

The present invention provides a new insect pest control agent that can instantly stop the movement of an insect pest and kill the insect pest, but that does not have a risk of explosion or ignition and that does not destroy the ozone layer and that has a low global warming potential, and therefore that can be safely used.

An insect pest control agent comprising 1-chloro-3,3,3-trifluoropropene as an active agent solves the above problem.

23 Claims, 1 Drawing Sheet

(56) References Cited

U.S. PATENT DOCUMENTS

| 2010/0102272 A1* | 4/2010 | Basu | C08J 9/127 |
| | | | 252/182.12 |
| 2011/0000980 A1* | 1/2011 | Yamamoto | A01N 25/06 |
| | | | 239/337 |
| 2013/0052354 A1* | 2/2013 | Hulse | C10M 171/005 |
| | | | 427/384 |

FOREIGN PATENT DOCUMENTS

| JP | 04-120003 A | 4/1992 |
| JP | 04-321603 A | 11/1992 |
| JP | 09-309802 A | 12/1997 |
| JP | 2008-1333438 A | 6/2008 |
| JP | 2009-227662 A | 10/2009 |
| JP | 2010-077033 A | 4/2010 |
| JP | 2010-106021 A | 5/2010 |
| JP | 2011-037912 A | 2/2011 |
| JP | 2011-510119 A | 3/2011 |
| JP | 2011-046688 A | 10/2011 |
| WO | 2007002625 A2 | 1/2007 |
| WO | 2009089511 A2 | 7/2009 |
| WO | 2013028943 A2 | 2/2013 |

\* cited by examiner

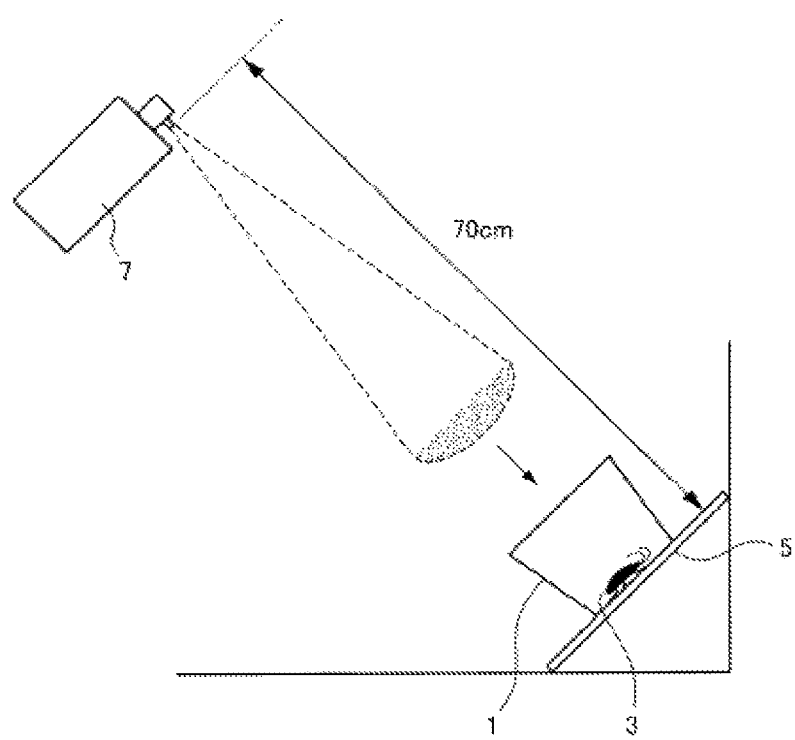

INSECT PEST CONTROL AGENT

TECHNICAL FIELD

The present invention relates to insect pest control agents and to methods of controlling insect pests and devices for controlling insect pests.

BACKGROUND ART

Chemically synthesized insecticides such as pyrethroid compounds, carbamate compounds and organophosphates have been used as active ingredients of insect pest control agents. More recently, various insect pest control agents using new types of active ingredients have been considered as demand for safer insecticides for human bodies and the like is rising.

Examples of new types of insect pest control agents include insecticides that can knockdown and kill insect pests by anesthetic action using at least one active ingredient selected from the hydrocarbons such as n-pentane, isopentane, cyclopentane (e.g. refer to Patent Document 1) and acaricides to eliminate mites and house dust mites and the like by using fluorinated alkanes which are volatile at normal temperature, such as flon 22 or flon 123, as a gas by vaporization or fine particulates of a liquid in a sealed space (e.g. refer to Patent Document 2).

CITATION LIST

Patent Documents

Patent Document 1: Japanese unexamined patent publication No. 04-120003A (pages 1-8)
Patent Document 2: Japanese unexamined patent publication No. 04-321603A (pages 1-10)

SUMMARY OF INVENTION

Problem to be Solved by the Invention

The hydrocarbons such as pentanes have a disadvantages in certain applications because they do not exhibit sufficient insecticidal effect, and in many cases such materials have the substantial deficiency of the high potential for ignition and explosion, which makes them especially disadvantageous for indoor use. Furthermore, the fluorine-substitued alkanes, which are volatile at normal temperature, are acknowledged as a cause of ozone depletion and as a result their use is regulated, moreover, the use of such compounds is limited to use in the elimination of mites.

One object of the present invention is to provide new insect pest control agents, insect pest control devices, and insect control methods that provide advantage over certain of the previously used pest control agents, such as by reducing or eliminating the risk of explosion or ignition and/or by being more environmentally friendly.

Solution to Problem

The present inventors arrived at the present invention by a dedicated study to improve on certain previously used insect pest control agents and have found that advantage can be achieved by insect pest control agents comprising an active ingredient comprising 1-chloro-3,3,3-trifluoropropene and that such insect pest control agent can be used in devices and methods to stop the movement of an insect pest and/or kill the insect pest.

That is to say, the present invention can be achieved by (1) to (17) below.

(1) An insect pest control agent comprising 1-chloro-3,3,3-trifluoropropene as an active ingredient.

(2) The insect pest control agent according to (1) further comprises a propellant.

(3) The insect pest control agent according to (2), wherein said propellant is at least one of dimethyl ether, liquefied petroleum gas, 1,3,3,3-tetrafluoropropene (HFO-1234ze) and combinations thereof.

(4) The insect pest control agent according to any one of (1) to (3) wherein the insect pest control agent is an aerosol agent.

(5) The insect pest control agent according to any one of (1) to (4), wherein said insect pest control agent does not contain azeotropic or azeotropic-like composition comprising methyl iodide.

(6) A method of controlling an insect pest comprising
(a) providing an insect pest control agent comprising an active ingredient comprising 1-chloro-3,3,3-trifluoropropene; and
(b) applying said insect pest control agent to the insect pest in an amount and under conditions effective to incapacitate and/or stop and/or kill the insect pest.

(7) The method of (6) wherein said applying step comprises spraying said insect pest control agent onto said insect pest.

(8) A method of (7), wherein the insect pest control agent contains 1-chloro-3,3,3-trifluoropropene as an active ingredient and at least one of dimethyl ether, liquefied petroleum gas, 1,3,3,3-tetrafluoropropene (HFO-1234ze) and combinations thereof as a propellant.

(9) The method according to (8) wherein the insect pest control agent is an aerosol agent.

(10) The method of (7) wherein said providing step comprises providing said insect pest control agent in a container having a nozzle for spraying the contents thereof.

(11) The method of (10) wherein said container is a pressure resistant container and said insect pest control agent further comprises a propellant for expelling said insect pest control agent from said container.

(12) The method of (11), wherein said propellant is at least one of dimethyl ether, liquefied petroleum gas, 1,3,3,3-tetrafluoropropene (HFO-1234ze) and combinations thereof.

(13) The method of (6) wherein said applying step comprises attaching said insect pest control agent comprising an active ingredient comprising 1-chloro-3,3,3-trifluoropropene to an insect pest.

(14) The method according to (13) wherein the insect pest control agent is attached in a liquid drop form to an insect pest.

(15) The method according to any one of (6) to (14), wherein said insect pest control agent does not contain azeotropic or azeotropic-like composition comprising methyl iodide.

(16) A device for incapacitating and/or stopping and/or killing an insect pest comprising
(a) a container; (b) an insect pest control agent in said container and comprising an active ingredient comprising 1-chloro-3,3,3-trifluoropropene and at least one additional insecticide; and (c) means attached to said container for applying said insect pest control agent to the insect pest.

(17) The device of (16) wherein said 1-chloro-3,3,3-trifluoropropene comprises trans-1-chloro-3,3,3-trifluoropropene.

Note that the capability of 1-chloro-3,3,3-trifluoropropene to instantly stop the movement of an insect pest and to kill the insect pest is a new finding, and the only usages considered conventionally for the ingredient were an extractant/solvent for biologically active compounds (International Published Application PCT/US2006/024886) and mineral oils, a refrigerant, a foaming agent composition, a solvent including a wash for electronic components, precision machinery components and the like and a methyliodide fumigant (For example, refer to Japanese Patent Unexamined Publication No. 2011-37912, Japanese Patent Unexamined Publication No. 2011-46688, Japanese Patent Unexamined Publication No. 2008-133438, Japanese Patent Unexamined Publication No.2010-106021, and Japanese Patent Unexamined Publication No.2011-510119).

Advantageous Effects of Invention

The insect pest control agents, devices and methods of the present invention can incapacitate, stop and/or kill the insect pest, and preferably do so very quickly, and even more preferably do so substantially instantly upon application of the pest control agent of the present invention to the insect pest. Hence, in preferred embodiments, insect pests with quick movements, such as a cockroach, can be incapacitated, stopped and/or killed upon a single application of the present control agent (such as spraying), and there is no need to pursue the insect pest to achieve a second application of the pest control agent to the insect pest. In preferred embodiments, therefore, insect pests can be incapacitated, stopped and/or killed, and preferably all three of these, by an application, and preferably a single application, of the pest control agent of the present invention, preferably by a applying a amount in accordance with the invention as described herein, of the pest control agent. In certain preferred embodiments, the desired effect described herein is achieved by an application of the present control agent to the insect which does not result in any substantial liquid residue being deposited upon the floor surface upon which the pest/insect had been located.

Further, the preferred pest control agent, devices and methods can incapacitate, stop and/or kill an insect/pest which is resistant to synthetic insecticides. Moreover, the insect pest control agents, methods and devices of the present invention can be used safely without the risk of explosion or ignition and without causing ozone depletion.

BRIEF DESCRIPTION OF DRAWINGS

FIG. 1 is a diagram to describe the test method.

EMBODIMENTS TO CARRY OUT THE INVENTION

The insect pest control agent of the present invention is described in detail below.

Note that the "active ingredient" of the present invention is an ingredient that is active with respect to and at least participates in, and preferably is primarily responsible for, the effect of incapacitating, stopping, killing or otherwise eliminating the insect pest.

The insect pest control agent of the present invention includes an active ingredient that comprises, preferably comprises in major proportion by weight, and even more preferably in certain embodiments consists essentially of 1-chloro-3,3,3-trifluoropropene ($CF_3CH=CHCl$: HFO-1233zd). HFO-1233zd is a known compound and under ambient conditions is a transparent liquid that is nontoxic and incombustible. Further, 1-chloro-3,3,3-trifluoropropene is easy to handle because it has high solubility to other ingredients such as solvents, has high stability, and dries quickly.

The ingredient 1-chloro-3,3,3-trifluoropropene can be used in accordance with the present invention in either of the existing isomeric forms, the cis form and the trans form, or a mixture of the two forms. In many embodiments it is preferable to use HFO-1233zd that comprises at least about 99% by weight of trans-1-chloro-3,3,3-trifluoropropene (trans-HFO-1233zd), and even more preferably consists of essentially 100% trans-1-chloro-3,3,3-trifluoropropene (trans-HFO-1233zd) which is highly effective in accordance with present invention and in preferred device and method embodiments is effective in quickly, and preferably substantially instantly, incapacitating and/or stopping the movement of an insect/pest.

In preferred embodiments of the present invention, the insect control agents, methods and devices of the present invention are formulated to achieve release of materials to the environment having an Ozone Depletion Potential (ODP) of less than 0.5, more preferably less than 0.1 and even more preferably of about zero. The use of trans-HFO-1233zd in accordance with the present invention is highly beneficial in this regard because it has an average Ozone Depletion Potential (ODP) of about zero. The ozone depletion potential (ODP) of a chemical compound is the relative amount of degradation to the ozone layer it can cause, with trichlorofluoromethane (R-11) being fixed at an ODP of 1.0. Chlorodifluoromethane (R-22), for example, has an ODP of 0.05.

In further preferred embodiments of the present invention, the insect control agents, methods and devices of the present invention are formulated to achieve release of materials to the environment having a Global Warming Potential (GWP) of less than about 150, and even more preferably less than about 75. The use of trans-HFO-1233zd in accordance with the present invention is highly beneficial in this regard because trans-HFO-1233zd has a 100-year Global Warming Potential (GWP) of less than 7. Global warming potential (GWP) is a measure of how much a given mass of greenhouse gas is estimated to contribute to global warming. It is a relative scale which compares the gas in question to that of the same mass of carbon dioxide, whose GWP is 1 by definition. A GWP is calculated over a specific time interval and the value of this must be stated whenever a GWP is quoted. The most common time interval used today is 100 years.

In certain embodiments, the insect pest control agent of the present invention comprises only active ingredient, and as mentioned above in certain preferred embodiments the active ingredient of the present insect pest control agent consists essentially of HFO-1233zd, and even more preferably trans-HFO-1233zd. In certain embodiments, the pest control agent comprises in addition to the active ingredient one or more other ingredients to achieve a desired feature of characteristic to the pest control agent, as explained in more detail below. However, it is generally preferred that the present insect pest control agent does not include any ingredient or component that would pose a risk of harm to humans or other animals. It is highly preferred, for example, that the pest control agent, devices and methods of the present invention do not include, incorporate or utilize any methyliodide.

According to method aspects of the present invention, the insect pest control agent of the present invention is applied to the pest insect, preferably so that it directly attaches to the insect pest. In some embodiments, the application step comprises pouring or dropping the pest control agent of the present invention onto the insect pest in liquid form, as an emulsion and the like, so that the agent attaches to the insect pest as a droplet. In certain preferred embodiments, the present methods comprise spraying the present insect pest control agent using a hydraulic accumulating sprayer or proving the agent in a device comprising a pressure resistant container and then discharging the insect pest control agent from the container and onto the insect pest, preferably by spraying the pest control agent in the form of an aerosol onto the insect pest.

Although applicant does not intend to be bound by or to any particular theory of operation, it is believed that the highly beneficial and fast-acting effect of the preferred forms of the present invention are achieved, at least in part, because HFO-1233zd, and preferably trans-HFO-1233zd, quickly removes from the insect essential materials, such as body oils, and that the rapid removal of these materials quickly incapacitates, stops and/or kills the insect. Furthermore, the present invention in preferred embodiments provides a dual-action which contributes to excellent and fast action. More specifically, in preferred embodiments as described in more detail hereinafter, the insect pest control agent includes, in addition to HFO-1233zd, a propellant in the form of a liquefied gas, preferably HFO-1234ze, and this is used to carry the active ingredient to the insect. In such preferred embodiments, the propellant serves to impart a rapid and substantial temperature reduction to the body of the insect as the propellant evaporates, and this effect interacts synergistically with the action of HFO-1233zd to achieve the exceptional and unexpected result reported herein.

In certain embodiments, therefore, the pest control agent comprises in addition to the active ingredient a propellant or an aerosol agent that enables the active ingredient to be applied quickly to a wide range of area, and such embodiments are especially preferable when insect pests with quick movements, such as a cockroach, are the target of the methods of the present invention. In general it is preferred that when the present insect pest control agent comprises two or more components, then such mixture of components are not in the form of azeotrope or azeotrope-like compositions.

For formulations including a liquid agent and aerosol agent, the active ingredient is contained in the insect pest control agent at an amount of preferably from 5 mass %, more preferably from 30 mass %, preferably to 70 mass %, more preferably to 50 mass %, to the entire agent.

When a liquid agent or a concentrate of an aerosol is prepared, a solvent can be used together with HFO-1233zd. The solvent is contained at an amount of preferably from 30 mass %, more preferably from 50, preferably to 95 mass % more preferably to 70 mass %, to the entire agent.

When an aerosol is prepared, any type of a propellant including a liquefied gas and a compressed gas such as carbon dioxide gas or nitrogen gas may be used together with HFO-1233zd. A liquefied gas propellant may be contained at an amount of preferably from 30 mass %, more preferably from 50 mass %, preferably to 95 mass %, more preferably to 70 mass %, to the entire agent. A compressed gas propellant having a pressure of preferably from 0.3 to 1 MPa may be used with the concentrate of the agent. A liquefied gas propellant and a compressed gas propellant may be used in combination.

The insect pest control agent of the present invention can be prepared as an aerosol agent by introducing the active ingredient into a container and providing a means or mechanism to discharge the active ingredient from the container under pressure. In certain embodiments, this comprises providing the container with a spray pump. In other embodiments, the pest control agent comprises a combination of the active ingredient and a propellant, each of which are charged into a pressure container equipped with a spraying means or nozzle. A typical active ingredient:propellant for a liquefied gas is 10-90:90-10 (volume ratio).

The present pest control agent may include, in addition to the active ingredient, other materials such as solvents, propellants or other ingredients. In certain preferred embodiments, the propellant when present may be any such material known to those skilled in the art as being usable in connection with pest control agents, and in certain embodiments is selected from: liquefied petroleum gas (LPG), such as propane, propylene, n-butane, isobutane; liquefied gas, such as dimethyl ether (DME), compressed gas such as carbonic acid gas, nitrogen gas, compressed air; halocarbon gas such as HFC-152a, HFC-134a, HFO-1234yf (GWP=4), HFO-1234ze (GWP=6), including preferably trans-HFO-1234ze, and combinations of any two or more of these. In certain embodiments, the propellant comprises at least one of dimethyl ether, liquefied petroleum gas and HFO-1234ze, since each of these may contribute significant knockdown and insecticide effects when combined with the HFO-1233zd of the present invention, with dimethyl ether being particularly preferable because it enhances the effect of instantly incapacitating, stopping or killing the insect pest.

Further, when the internal pressure of the aerosol agent is low, the internal pressure can be adjusted through pressurization by a compression gas.

Further, it is preferable to adjust conditions including the ratio of the active ingredient and the propellant, the pressure, and the specification of the spraying means to spray the aerosol agent at a rate of about 1-10 g/second.

Other ingredients for forming a formulation from the insect pest control agent of the present invention include one or two or more of water; solvents including alcohols such as isopropyl alcohol, ethanol, denatured alcohol, glycols such as propylene glycol, ethylene glycol, pentanes such as isopentane, normal pentane, paraffin hydrocarbons such as isoparaffin, normal paraffin, petroleums such as naphthenic hydrocarbon or kerosene, esters such as isopropyl myristate, hexyl laurate; solubilizers including lactate, alkyl pyrrolidone, polyvinyl pyrrolidone, carbonic acid ester, nonionic surfactant, cationic surfactant, anionic surfactant, amphoteric surfactant. These solvents and solubilizers can be included in a range that does not negate the effect of the present invention.

Further, one or two or more types of adjuvant such as bactericide, antiseptic, synergist, deodorant, aromatic may be used if necessary. The adjuvant can be included in a range that does not negate the effect of the present invention, preferably, not more than 5 mass %, in particular from 0.1 to 1 mass % with regard to the total mass of the entire agent.

Examples of bactericides and antiseptics include phenol compounds such as chloroxylenol, 3-methyl-4-isopropylphenol, thymol; quaternary ammonium compounds such as benzalkonium chloride, cetylpyridinium chloride; and 3-iodo-2-propynyl butylcarbamate, phenoxyethanol, triclosan, N-dichlorofluoromethylthio-N',N'-dimethyl-N-phenylsulfamid.

Examples of deodorants include plant extracts such as tea extracts, catechin, plant polyphenol; and lauryl methacrylate, geranylcrotonate, myristic acid acetophenone, paramethylacetophenone benzaldehyde.

Examples of aromatics include natural aromatics such as musk, bergamot oil, cinnamon oil, citronella oil, lemon oil, lemon glass oil; and artificial aromatics such as pinene, limonene, linalool, menthol, borneol, eugenol, citral, citronellal and geraniol.

Examples of synergists include piperonyl butoxide, octachlorodipropylether, N-(2-ethylhexyl)bicyclo-[2.2.1]-hept-5-ene-2,3-dicarboximide.

Further, the insect pest control agent of the present invention does not necessarily require an insecticidal component and a repelling component to be included, but an insecticidal component (insecticide) or a repelling component (repellent) may be used if desired. However, from the viewpoint of environmental issues, the present insect pest control agent do not contain methyl iodide. The insecticidal component and the repelling component can be included in a range that does not negate the effect of the present invention, for example, not more than 10 mass %, in particular from 0.01 to 5 mass % with regard to the total mass of the present composition.

Examples of insecticides and repellents include pyrethroid compounds such as natural pyrethrin, allethrin, resmethrin, furamethrin, prallethrin, terallethrin, phthalthrin, phenothrin, permethrin, cyphenothrin, transfluthrin, metofluthrin, profluthrin, empenthrin, imiprothrin and ethofenprox; carbamate compounds such as propoxur and carbaryl; organophosphine compounds such as fenitrothion and DDVP; oxadiazol compounds such as metoxadiazone; neonicotinoid compounds such as dinotefuran, imidacloprid and acetamiprid; insect growth regulators such as methoprene, hydroprene and pyriproxyfen; phenylpyrazole compounds such as fipronil and pyriprole; pyrrole compounds such as chlorfenapyr; sulfonamide compounds such as amidoflumet; and essential oils with insecticidal or repelling properties such as phytoncide, peppermint oil, orange oil, cinnamon oil and clove oil.

Examples of the composition of the present insect pest control agent includes:
a composition comprising:
(a) preferably from 5 mass %, more preferably from 30 mass %, preferably to 70 mass %, more preferably to 50 mass % of HFO-1233zd, in particular trans-HFO-1233zd;
(b) optionally, preferably from 30 mass %, more preferably from 50 mass %, preferably to 95 mass %, more preferably to 70 mass % of solvent, in particular kerosene;
(c) optionally, not more than 10 mass %, preferably 0.01 to 5 mass % of at least one of insecticidal component and the repelling component; and
(d) optionally, not more than 5 mass %, preferably 0.1 to 1 mass % of at least one of other adjuvants,
with regard to 100 mass % of the total amount of the composition.

When a liquefied gas propellant is used, examples of the aerosol composition of the present insect pest control agent includes:
an aerosol composition comprising:
(a) preferably from 5 mass %, more preferably from 30 mass %, preferably to 70 mass %, more preferably to 50 mass % of HFO-1233zd, in particular trans-HFO-1233zd;
(b) preferably from 30 mass %, more preferably from 50 mass %, preferably to 95 mass %, more preferably to 70 mass % of a liquefied gas propellant, in particular at least one of dimethyl ether, liquefied petroleum gas and 1,3,3,3-tetrafluoropropene (HFO-1234ze);
(c) optionally, preferably from 30 mass %, more preferably from 50 mass %, preferably to 95 mass %, more preferably to 70 mass % of solvent, in particular kerosene;
(d) optionally, not more than 10 mass %, preferably 0.01 to 5 mass % of at least one of insecticidal component and the repelling component; and
(e) optionally, not more than 5 mass %, preferably 0.1 to 1 mass % of at least one of other adjuvants,
with regard to 100 mass % of the total amount of the composition.

When a compressed gas propellant is used to form an aerosol composition, the aerosol composition contains the concentrate and the compressed gas propellant. The examples of the aerosol composition of the present insect pest control agent includes:
an aerosol composition comprising:
(i) a concentrate comprising:
(a) preferably from 5 mass %, more preferably from 30 mass %, preferably to 70 mass %, more preferably to 50 mass % of HFO-1233zd, in particular trans-HFO-1233zd;
(b) optionally, preferably from 30 mass %, more preferably from 50 mass %, preferably to 95 mass %, more preferably to 70 mass % of a liquefied gas propellant, in particular at least one of dimethyl ether, liquefied petroleum gas and 1,3,3,3-tetrafluoropropene (HFO-1234ze);
(c) optionally, preferably from 30 mass %, more preferably from 50 mass %, preferably to 95 mass %, more preferably to 70 mass % of solvent, in particular kerosene;
(d) optionally, not more than 10 mass %, preferably 0.01 to 5 mass % of at least one of insecticidal component and the repelling component; and
(e) optionally, not more than 5 mass %, preferably 0.1 to 1 mass % of at least one of other adjuvants,
with regard to 100 mass % of the total amount of the concentrate; and
(ii) a compressed gas propellant having a pressure of preferably from 0.3 to 1 MPa.

Insect pests targeted by the insect pest control agent of the present invention is not limited as long as the invention can be effectively used, but examples include cockroaches, centipedes, millipedes, a house centipede, a pillbug, a wood louse, ants such as *Pristomyrmex punctatus*, spiders such as *Latrodectus hasseltii*, flies, mosquitoes, bees, moths, thaumaleidaes, leafhoppers, pentatomidaes, mites, caterpillars, termites, fruit flies, moth flies, and bed bugs. The present invention is especially suitable for use against cockroaches having quick movements, and spiders, ants and bed bugs that cause harm to humans by their sting and bite.

EXAMPLES

The present invention is described in detail by the Examples below. Note that the present invention is not limited by these Examples.

Specific gravities of the materials used in the following examples are as follows:
(Specific Gravities)
trans-1-chloro-3,3,3-trifluoropropene (trans-HFO-1233zd): 1.30 g/cm$^3$ at 20° C.
GALDEN SV80: 1.70 g/cm$^3$ at 25° C.
ASAHIKLIN AC2000: 1.67 g/cm$^3$ at 25° C.
dimethyl ether: 0.66 g/cm$^3$ at 20° C.

liquefied petroleum gas (3 Kg): 0.56 g/cm³ at 20° C.
HFO-1234ze: 1.19 g/cm³ at 20° C.
kerosene: 0.756 g/cm³ at 20° C.

<Measuring the Flash Point>

The flash point was measured using a tag closed cup flash point tester (JIS K2265-1) by preparing solutions with 20, 30, 35, 40 mass % of ethanol mixed in trans-l-chloro-3,3,3-trifluoropropene.

The result was that the solutions did not ignite during measurement, and all solutions had no flash point. Thus, the solutions corresponded to "non-hazardous material" in the Fire Service Act.

<Efficacy Test 1: Concentrate Dropping Test>

(1) Test Method

A plastic cup (capacity of 860 ml) that is open at the top was provided, and butter was spread on the upper part of the cup interior. Then, as a subject insect, one female cockroach (periplaneta fuliginosa) was gently placed on its back at the bottom of the plastic cup.

After confirming that the subject insect is lying on its back, 0.5 mL of the subject agent in Table 1 was dropped on to the insect between the thorax and the abdomen using a pipet, and the time (seconds) until the subject insect's movement completely stopped was measured.

Subsequently, the subject insect was transferred to another plastic cup and left in a room having a temperature of 20° C. and a humidity of 26%. The number of subject insects that died after 24 hours was counted. The test was repeated five times to obtain the lethality (%) based on the average of the results. Table 2 shows the test result.

TABLE 2

|  | Time until the subject insect stops moving (seconds) | | | | | | Lethality (%) after 24 hours |
| --- | --- | --- | --- | --- | --- | --- | --- |
|  | No. 1 | No. 2 | No. 3 | No. 4 | No. 5 | Average |  |
| Example 1 | 2 | 1 | 1 | 1 | 2 | 1.4 | 80 |
| Comparative Example 1 | 55 | 62 | 46 | 50 | 49 | 52.4 | 20 |
| Comparative Example 2 | 54 | 50 | 53 | 62 | 63 | 56.4 | 40 |

(2) Test Result

As shown in Table 2, the time it took for the subject insect to stop moving in Example 1 averaged 1.4 seconds. The time was extremely short compared to the time it took for the subject insect to stop moving in Comparative Examples 1 and 2. The result showed that the ingredient of the present invention has a high fast-acting property to instantly stop the subject insect's movement. Further, Example 1 showed high lethality (%) after 24 hours, and it exhibited excellent insect pest control effects.

<Efficacy Test 2: Aerosol Efficacy Test>

(1) Test Specimen

A concentrate of the active ingredient and a propellant (dimethyl ether, liquefied petroleum gas and trans-HFO-1234ze) according to the recipe of Table 3, were filled in the aerosol pressure can (capacity of 300 ml) equipped with a spraying device (stem bore 0.6 mm, under tap bore 2.2 mm, button bore for spraying 1.5 mm×4 holes) to obtain a test specimen in the form of an aerosol agent. The aerosol agents were each sprayed at a rate of about 4 g/second.

TABLE 3

|  |  | Test Specimen | | | | |
| --- | --- | --- | --- | --- | --- | --- |
|  |  | Example 2 | Example 2-1 | Example 2-2 | Comparative Example 3 | Comparative Example 4 |
| Concentrate | Trans-1-chloro-3,3,3-trifluoropropene | 100 mL | 100 mL | 100 mL | — | — |
|  | GALDEN SV80 (Product Name, produced by SOLVAY SOLEXIS S.p.A)(*1) | — | — | — | 100 mL | — |
|  | ASAHIKLIN AC-2000 (Product Name, produced by Asahi Glass)(*2) | — | — | — | — | 100 mL |
| Propellant | Dimethyl ether | 200 mL | — | — | 200 mL | 200 mL |
|  | Liquefied Petroleum Gas (LPG 3.0) | — | 200 mL | — | — | — |
|  | trans-HFO-1234ze | — | — | 200 mL | — | — |
|  | Total |  |  | 300 mL |  |  |

(*1)Perfluoropolyether
(*2)1H-Tridecafluorohexane

TABLE 1

| Subject Agents | |
| --- | --- |
| Example 1 | Trans-1-chloro-3,3,3-trifluoropropene |
| Comparative Example 1 | GALDEN SV80 (Product Name, produced by SOLVAY SOLEXIS S.p.A)(*1) |
| Comparative Example 2 | ASAHIKLIN AC-2000 (Product Name, produced by Asahi Glass)(*2) |

(*1)Perfluoropolyether
(*2)1H-Tridecafluorohexane (2) Test Method

As shown in FIG. 1, plastic cup 1 (a plastic cup having a capacity of 860 ml and open at the top, wherein butter is spread on the upper part of the cup interior) with a subject insect 3 (one female cockroach (periplaneta fuliginosa)) inside it was prepared and arranged on a platform 5 at a tilt angle of 45° to be on the line that the sprayed aerosol agent (test specimen) 7 travels. The aerosol agent 7 was sprayed for two seconds to the center of the plastic cup 1 from about 70 cm away from the center of the bottom of the plastic cup 1.

Just after the spraying, the subject insect 3 was transferred to another plastic cup and the time (seconds) until it was knocked down was measured. Subsequently, the subject insect was transferred to another plastic cup and left in a room having a temperature of 20° C. and a humidity of 26%.

The number of subject insects that died after 24 hours were counted. The test was repeated five times to obtain the lethality (%) based on the average of the results. If the subject insect was not knocked down for 5 minutes or longer, it was determined as "not knocked down". Table 4 shows the test result.

TABLE 4

|  | Example 2 | Example 2-1 | Example 2-2 | Comparative Example 3 | Comparative Example 4 |
|---|---|---|---|---|---|
| Time until knockdown (sec) | less than 1 sec. | less than 1 sec. | less than 1 sec. | not knocked down | not knocked down |
| Lethality(%) after 24 hours | 100% | 100% | 100% | 0% | 0% |

(3) Test Result

As shown in Table 4, the subject insect was knocked down within 1 second in Examples 2, 2-1 and 2-2, showing an extremely high fast-acting property. Further, the lethality (%) after 24 hours was 100%, showing sufficient lethal effects. On the other hand, Comparative Examples 3 and 4 showed no knock downs or death after 24 hours.

The above tests provide the understanding that the ingredient of the present invention shows excellent knockdown effects and lethal effects when it is used as an aerosol agent.

<Efficacy Test 3>

(1) Test Specimen

A concentrate (active ingredient, solvent) and a propellant (dimethyl ether, carbonic acid gas, liquefied petroleum gas and trans-HFO-1234ze) according to the recipe of Table 5, were filled in the aerosol pressure can (capacity of 300 ml) equipped with a spraying device (stem bore 0.6 mm, under tap bore 2.2 mm, button bore for spraying 1 5 mm×4 holes) to obtain a test specimen in the form of an aerosol agent. The aerosol agents of Examples 3 to 5 were sprayed at a rate of about 5 g/second, and the aerosol agents of Examples 6, 7 were sprayed at a rate of about 4 g/seconds, and the aerosol agents of Examples 8, 8-1, 8-2 and 9 were sprayed at a rate of about 3 g/seconds.

(2) Test Method

A subject insect (one female cockroach (periplaneta fuliginosa)) was released in the test room (about 8 tatami-mat space, temperature of 26° C., humidity of 56%) and the test specimen was sprayed to the insect from about 70 cm away until the insect was knocked down.

The time until the subject insect was knocked down was measured, and the wetness of the test room floor where the test specimen was applied was confirmed. The tests were all repeated 3 times, and the result of the assessment was shown in Table 6.

Knockdown was assessed as follows: "○" was assigned when all subject insects in all of the 3 times were knocked down within 5 seconds and "Δ" was assigned when all subject insects in all of the 3 times were knocked down within 10 seconds.

Wetness was assessed as follows: "○" was assigned when almost no wetness from the test specimen was seen at the sprayed area and "Δ" was assigned when a little wetness was seen.

TABLE 6

| Assessment Items | Test Specimen | | | | | | | | |
|---|---|---|---|---|---|---|---|---|---|
|  | Example 3 | Example 4 | Example 5 | Example 6 | Example 7 | Example 8 | Example 8-1 | Example 8-2 | Example 9 |
| Knockdown | ○ | ○ | ○ | ○ | ○ | ○ | ○ | ○ | Δ |
| Floor wetness | ○ | Δ | Δ | Δ | Δ | ○ | ○ | ○ | ○ |

(3) Test Result

As shown in Table 6, the subject insect was knocked down within 10 seconds in Examples 3 to 9 which are aerosol agents of the present invention, showing an extremely high fast-acting property. Especially in Examples 3 to 8, and 8-1 and 8-2, the subject insects were knocked down within 5 seconds, which shows an especially high fast-acting property. Further, the floor showed a little wetness or almost no wetness. Hence, the aerosol agents were assessed as having good usability.

<Efficacy Test 4>

(1) Test Specimen

A concentrate of the active ingredient (trans-1-chloro-3, 3,3-trifluoropropene) and a propellant (dimethyl ether) according to the recipe of Table 7, were filled in the aerosol pressure can (capacity of 300 ml) equipped with a spraying device (stem bore 0.6 mm, under tap bore 2.2 mm, button bore for spraying 1.5 mm×4 holes) to obtain a test specimen in the form of an aerosol agent. The aerosol agents were each sprayed at a rate of about 4 g/second.

TABLE 5

|  |  | Test Specimen | | | | | | | | |
|---|---|---|---|---|---|---|---|---|---|---|
|  |  | Example 3 | Example 4 | Example 5 | Example 6 | Example 7 | Example 8 | Example 8-1 | Example 8-2 | Example 9 |
| Concentrate | Trans-1-chloro-3,3,3-trifluoropropene | 200 mL | 100 mL | 60 mL | 75 mL | 45 mL | 50 mL | 50 mL | 50 mL | 30 mL |
|  | Kerosene | — | 100 mL | 140 mL | 75 mL | 105 mL | 50 mL | 50 mL | 50 mL | 70 mL |
| Propellant | Dimethyl ether | 100 mL | 100 mL | 100 mL | 150 mL | 150 mL | 200 mL | — | — | 200 mL |
|  | Liquefied Petroleum Gas (LPG3.0) | — | — | — | — | — | — | 200 mL | — | — |
|  | trans-HFO-1234ze | — | — | — | — | — | — | — | 200 mL | — |
|  | Carbonic Acid Gas | 0.55 MPa | 0.55 MPa | 0.55 MPa | — | — | — | — | — | — |
| Total |  | 300 mL | | | | | | | | |

TABLE 7

| | Test Specimen |
|---|---|
| trans-1-chloro-3,3,3-trifluoropropene | 100 mL |
| dimethyl ether | 200 mL |
| Total | 300 mL |

(2) Test Method

As shown in FIG. 1, plastic cup 1 (a plastic cup having a capacity of 860 ml and open at the top, wherein butter is spread on the upper part of the cup interior) with a subject insect 3 shown in Table 8 inside it was prepared and arranged on a platform 5 at a tilt angle of 45° to be on the line that the sprayed aerosol agent (test specimen) 7 travels. The aerosol agent 7 was sprayed for one second to the center of the plastic cup 1 from about 70 cm away from the center of the bottom of the plastic cup 1.

Just after the spraying, the subject insect 3 was transferred to another plastic cup and the time (seconds) until it was knocked down was measured. Subsequently, the subject insect was transferred to another plastic cup and left in a room having a temperature of 20° C. and a humidity of 26%. The number of subject insects that died after 24 hours were counted. The test was repeated 3 times.

TABLE 8

| Subject Insect | Number of Subject Insect (Number per one time) |
|---|---|
| Latrodectus hasseltii | 1 head |
| Pristomyrmex punctatus | 5 heads |
| bed bugs | 1 head |

(3) Test Result

All of the subject insects in the 3 times were knocked down within 1 second (All of 5 heads of *Pristomyrmex punctatus* were knocked down within 1 second.), showing an extremely high fast-acting property. Further, all of the subject insects in the 3 times were died within 24 hours (All of 5 heads of *Pristomyrmex punctatus* were died within 24 hours).

EMBODIMENTS OF THE INVENTION

The present invention further includes the following embodiments.

[1] A method of controlling an insect pest comprising (a) providing an insect pest control agent comprising an active ingredient comprising 1-chloro-3,3,3-trifluoropropene; and (b) applying said insect pest control agent to the insect pest in an amount and under conditions effective to incapacitate and/or stop and/or kill the insect pest.

[2] The method of above [1] wherein said applying step comprises spraying said insect pest control agent onto said insect pest.

[3] The method of above [2] wherein said providing step comprises providing said insect pest control agent in a container having a nozzle for spraying the contents thereof.

[4] The method of above [3] wherein said container is a pressure resistant container and said insect pest control agent further comprises a propellant for expelling said pest control agent from said container.

[5] The method of above [4] wherein said propellant comprises HFO-1234ze.

[6] The method of above [5] wherein said HFO-1234ze is present in the container in the form of a liquefied gas.

[7] The method of above [1] wherein said applying step is effective to substantially instantly incapacitate and/or stop the movement of and/or kill the insect pest.

[8] The method of above [7] wherein said applying step comprises applying said insect pest control agent at a rate of from about 1 to about 10 gram per second.

[9] The method of above [7] wherein said applying step comprises spraying said insect pest control agent at a rate of from about 1 to about 10 gram per second.

[10] The method of above [7] wherein said applying step comprises spraying said insect pest control agent at a rate of from about 1 to about 10 gram per second and said insect pest is stopped in less than about 10 seconds after said applying step.

[11] The method of above [7] wherein said applying step comprises spraying said insect pest control agent at a rate of from about 1 to about 10 gram per second and said insect pest is stopped in less than about 2 seconds after said applying step.

[12] The method of above [7] wherein said applying step comprises spraying said insect pest control agent at a rate of from about 1 to about 10 gram per second and said insect pest is stopped in less than about 1 second after said applying step.

[13] The method of above [1] wherein said insect pest control agent is not an azeotropic or azeotropic-like composition.

[14] The method of above [1] wherein said insect pest control agent is not azeotropic or azeotropic-like composition comprising methyl iodide.

[15] The method of above [4], wherein said propellant is at least one of dimethyl ether, liquefied petroleum gas, 1,3,3,3-tetrafluoropropene (HFO-1234ze) and combinations of these.

[16] The method of any of above [1] to [15] wherein the insect pest control agent is applied in the form of an aerosol.

[17] Use as an active ingredient in an insect pest control agent of 1-chloro-3,3,3-trifluoropropene.

[18] The use of above [17] wherein said 1-chloro-3,3,3-trifluoropropene comprises trans-1-chloro-3,3,3-trifluoropropene.

[19] A device for incapacitating and/or stopping and/or killing an insect pest comprising (a) a container; (b) an insect pest control agent in said container and comprising an active ingredient comprising 1-chloro-3,3,3-trifluoropropene and at least one additional insecticide; and (c) means attached to said container for applying said insect pest control agent to the insect pest.

[20] The device of above [19] wherein said 1-chloro-3,3,3-trifluoropropene comprises trans -1-chloro-3,3,3-trifluoropropene.

[21] A method of controlling an insect pest comprising (a) providing an insect pest control agent comprising an active ingredient comprising 1-chloro-3,3,3-trifluoropropene and not comprising methyl iodide; and (b) applying said insect pest control agent to the insect pest in an amount and under conditions effective to incapacitate and/or stop and/or kill the insect pest.

[22] A method of controlling an insect pest comprising (a) providing an insect pest control agent comprising an active ingredient comprising a zoetropic mixture that includes 1-chloro-3,3,3-trifluoropropene and not comprising any substantial amount of methyl iodide; and (b) applying said insect pest control agent to the insect in an amount and under conditions effective to incapacitate and/or stop and/or kill the insect pest.

[23] A method of controlling an insect comprising (a) providing an insect pest control agent comprising an active ingredient comprising 1-chloro-3,3,3-trifluoropropene in a form that is not part of an azeotropic mixture and is not part of a mixture that behaves like an azeotropic mixture; and (b) applying said insect pest control agent to the insect pest in an amount and under conditions effective to incapacitate and/or stop and/or kill the insect pest.

[24] The method of above [23] wherein said 1-chloro-3,3,3-trifluoropropene is not in a mixture with from about 5 to about 70 weight percent of methyl iodide, or from about 15 to about 60 weight percent methyl iodide, or from about 25 to about 50 weight percent methyl iodide.

[25] The method of above [23] wherein said 1-chloro-3,3,3-trifluoropropene is not in a mixture with methyl iodide that boils at 14.5 psia in a range from about 8° C. to about 14.5° C., or from about 8° C. to about 13.8° C., or from about 8° C. to about 12.7° C.

[26] An insect pest control agent comprising an active ingredient comprising 1-chloro-3,3,3-trifluoropropene and not comprising any substantial amount of methyl iodide.

[27] An insect pest control agent comprising an active ingredient comprising a zoetropic mixture that includes 1-chloro-3,3,3-trifluoropropene and not comprising any substantial amount of methyl iodide.

[28] An insect pest control agent comprising an active ingredient comprising 1-chloro-3,3,3-trifluoropropene in a form that is not part of an azeotropic mixture and is not part of a mixture that behaves like an azeotropic mixture.

[29] The insect pest control agent of above [28] wherein said 1-chloro-3,3,3-trifluoropropene is not in a mixture with from about 5 to about 70 weight percent of methyl iodide, or from about 15 to about 60 weight percent methyl iodide, or from about 25 to about 50 weight percent methyl iodide.

[30] The insect pest control agent of above [28] wherein said 1-chloro-3,3,3-trifluoropropene is not in a mixture with methyl iodide that boils at 14.5 psia in a range from about 8° C. to about 14.5° C., or from about 8° C. to about 13.8° C., or from about 8° C. to about 12.7° C.

REFERENCE SIGNS LIST

1 Plastic cup
3 Subject insect
5 Platform
7 Aerosol agent

The invention claimed is:

1. An insect pest control agent comprising 1-chloro-3,3,3-trifluoropropene as an active ingredient, wherein said insect pest control agent does not contain an azeotropic or azeotrope-like composition comprising methyl iodide.

2. The insect pest control agent according to claim 1 further comprising a propellant.

3. The insect pest control agent according to claim 2, wherein said propellant is at least one of dimethyl ether, liquefied petroleum gas, 1,3,3,3-tetrafluoropropene (HFO-1234ze) and combinations thereof.

4. The insect pest control agent according to claim 1 wherein the insect pest control agent is an aerosol agent.

5. The pest control agent of claim 1 wherein said 1-chloro-3,3,3-trifluoropropene comprises of trans-1-chloro-3,3,3-trifluoropropene.

6. The pest control agent of claim 1 wherein said 1-chloro-3,3,3-trifluoropropene consists essentially of trans-1-chloro-3,3,3-trifluoropropene.

7. The pest control agent of claim 1 wherein said 1-chloro-3,3,3-trifluoropropene consists of trans-1-chloro-3,3,3-trifluoropropene.

8. A method of controlling an insect pest comprising
  (a) providing an insect pest control agent comprising an active ingredient comprising 1-chloro-3,3,3-trifluoropropene, wherein said insect pest control agent does not contain an azeotropic or azeotrope-like composition comprising methyl iodide; and
  (b) applying said insect pest control agent to the insect pest in an amount and under conditions effective to incapacitate and/or stop and/or kill the insect.

9. The method of claim 8 wherein said applying step comprises spraying said insect pest control agent onto said insect pest.

10. A method of claim 9, wherein the insect pest control agent further comprises at least one of dimethyl ether, liquefied petroleum gas, 1,3,3,3-tetrafluoropropene (HFO-1234ze) and combinations thereof as a propellant.

11. The method according to claim 10 wherein the insect pest control agent is an aerosol agent.

12. The method of claim 9 wherein said providing step comprises providing said insect pest control agent in a container having a nozzle for spraying the contents thereof.

13. The method of claim 12 wherein said container is a pressurized container and said insect pest control agent further comprises a propellant for expelling said insect pest control agent from said container.

14. The method of claim 13, wherein said propellant is at least one of dimethyl ether, liquefied petroleum gas, 1,3,3,3-tetrafluoropropene (HFO-1234ze) and combinations thereof.

15. The method of claim 8 wherein said applying step comprises applying said insect pest control agent to an insect pest.

16. The method according to claim 15 wherein the insect pest control agent is applied in a drop form to an insect pest.

17. The method of claim 8 wherein said 1-chloro-3,3,3-trifluoropropene comprises of trans-1-chloro-3,3,3-trifluoropropene.

18. The method of claim 8 wherein said 1-chloro-3,3,3-trifluoropropene consists essentially of trans-1-chloro-3,3,3-trifluoropropene.

19. The method of claim 8 wherein said 1-chloro-3,3,3-trifluoropropene consists of trans-1-chloro-3,3,3-trifluoropropene.

20. A device for incapacitating and/or stopping and/or killing an insect pest comprising (a) a container; (b) an insect pest control agent in said container and comprising an active ingredient comprising 1-chloro-3,3,3-trifluoropropene, wherein said insect pest control agent does not contain an azeotropic or azeotrope-like composition comprising methyl iodide and at least one additional insecticide; and (c) means attached to said container for applying said insect pest control agent to the insect pest.

21. The device of claim 20 wherein said 1-chloro-3,3,3-trifluoropropene comprises trans-1-chloro-3,3,3-trifluoropropene.

22. The device of claim 20 wherein said 1-chloro-3,3,3-trifluoropropene consists essentially of trans-1-chloro-3,3,3-trifluoropropene.

23. The device of claim 20 wherein said 1-chloro-3,3,3-trifluoropropene consists of trans-1-chloro-3,3,3-trifluoropropene.

\* \* \* \* \*